United States Patent [19]

Minamizono et al.

[11] 4,251,626

[45] Feb. 17, 1981

[54] SILVER HALIDE PHOTOGRAPHIC MATERIALS CONTAINING GELATIN REACTIVE ANTISTATIC AGENTS

[75] Inventors: Junji Minamizono; Masakazu Yoneyama; Shinzo Kishimoto, all of Minami-ashigara, Japan

[73] Assignee: Fuji Photo Film Co., Ltd., Minami-ashigara, Japan

[21] Appl. No.: 115,314

[22] Filed: Jan. 25, 1980

[30] Foreign Application Priority Data

Jan. 25, 1979 [JP] Japan .................................. 54/7946
Nov. 21, 1979 [JP] Japan .................................. 54/150874

[51] Int. Cl.³ .......................... G03C 1/02; G03C 1/78
[52] U.S. Cl. .................................... 430/527; 430/528; 430/529; 430/631
[58] Field of Search ............... 430/527, 528, 529, 631, 430/635, 640

[56] References Cited

U.S. PATENT DOCUMENTS

| | | |
|---|---|---|
| 2,882,157 | 4/1959 | Thompson et al. ............ 430/527 |
| 2,972,537 | 2/1961 | Laakso et al. ................. 430/527 |
| 3,547,643 | 12/1970 | Pechmann ..................... 430/528 |
| 3,607,286 | 9/1971 | Wood .............................. 430/527 |
| 3,708,289 | 1/1973 | Timmerman et al. ......... 430/527 |

*Primary Examiner*—Jack P. Brammer
*Attorney, Agent, or Firm*—Sughrue, Rothwell, Mion, Zinn and Macpeak

[57] ABSTRACT

A silver halide photographic material having on a support at least one gelatin-containing layer containing as an antistatic agent a gelatin reactive surface active agent having at least one long chain hydrophobic group, at least one of a hydrophilic group selected from a cationic group, an anionic group, an amphoteric and a nonionic group, and at least one group reactive with gelatin in the molecule.

8 Claims, No Drawings

SILVER HALIDE PHOTOGRAPHIC MATERIALS CONTAINING GELATIN REACTIVE ANTISTATIC AGENTS

BACKGROUND OF THE INVENTION

1. Field of the Invention

This invention relates to silver halide photographic materials and, more particularly, to silver halide photographic materials having improved antistatic property without adversely influencing the photographic properties thereof.

2. Description of the Prior Art

A photographic material is composed of a support and silver halide photographic emulsion layers each having electric insulating property and hence it frequently occurs that electrostatic charges are accumulated when photographic materials are brought into contact with or are separated from the surfaces of the same photographic material or foreign materials during the production steps or the use of the photographic materials. The accumulated electrostatic charge causes various undesirable problems. For example, in undeveloped photographic films, the photosensitive silver halide emulsion layers of the photographic materials are exposed to the discharge light (spark) of the accumulated electrostatic charge when discharging of the electrostatic charge occurs and spot-like, branch-like or feather-like marks appear when the photographic films are developed. These marks are called "static marks" and the commercial value of photographic films is greatly reduced or is wholly lost as the case may be with the occurrence of the static marks. If such marks appear in medical or industrial X-ray films, etc., it may cause a misdiagnosis as will be easily recognized. This is a very troublesome problem since the occurrence of static marks can only be discovered after the photographic materials have been developed. Also, static charge which accumulates on film supports during production causes dust to attach to the surface of the film support, which induces secondary problems such as uneven coating, etc.

Such electrostatic charges frequently accumulate during the production or use of photographic materials as described above. For example, in the production of photographic films, electrostatic friction generates charges upon contact of the photographic films with rollers or upon the separation of support surfaces from the surfaces of silver halide emulsion layers during winding or rewinding of the photographic films. Also, in finished photographic films, electrostatic charges are caused by the separation of base surfaces from the surfaces of silver halide emulsion layers when the photographic films are wound up at a high humidity condition. In X-ray films electrostatic charges are caused by the contact or separation of X-ray films and mechanical parts or fluorescent screens in automatic X-ray cameras. Still further, electrostatic charges are also generated upon contact of photographic films with packing materials. The occurrence of static marks in photographic materials induced by the accumulation of such electrostatic charges becomes more severe when the sensitivity of the photographic materials is increased and the processing speed for photographic materials is increased.

The frictional charging is considered due to the electronic or ionic interaction of materials in contact but it is difficult at present to sufficiently anticipate based on structural chemistry what type of material will charge positively or negatively. However, it is clear that the occurrence of such charging can be prevented by reducing the charge potential or by increasing the electric conductivity of the surfaces of the materials such that electrostatic charges are released in a very short period of time prior to the occurrence of partial discharging of the accumulated charge. Therefore, processes for increasing the conductivity of the supports and various coating surfaces of photographic materials have been proposed and the utilization of various hygroscopic materials and water-soluble inorganic salts as well as certain kinds of surface active agents, polymers, etc., has been attempted. For example, there are known for the purpose the polymers described in U.S. Pat. Nos. 2,882,157, 2,972,535, 3,062,785, 3,262,807, 3,514,291 and 3,615,531; the surface active agents described in British Pat. No. 861,134 and U.S. Pat. Nos. 2,982,651, 3,428,456, 3,457,076, 3,454,625, 3,552,972 and 3,655,387; and zinc oxide, the semiconductors and colloidal silica, etc., as described in U.S. Pat. Nos. 3,062,700, 3,245,833 and 3,525,621.

As a process of directly imparting antistatic property to the supports for photographic films, there are known processes wherein the above-described materials are directly incorporated in the polymers used as supports for photographic films or are coated on the surfaces of the supports. In the latter case, the antistatic agents are coated on the supports for photographic materials as backing layers solely or as a combination with a polymer such as gelatin, polyvinyl alcohol, cellulose acetate, etc. Also, as an antistatic process for photographic materials, there is a process wherein the antistatic agent is incorporated in the photographic silver halide emulsion layers or the surface protective layers of the photographic materials or a solution of the antistatic agent is coated on the surfaces of these layers. However, the many antistatic materials as described above each show specificity according to the kind of film support used and the different photographic compositions and it sometimes occurs that they may show good results for one specific film support, photographic silver halide emulsion, and other photographic constituting elements but are utterly useless for the static prevention of other different film supports and photographic constituting elements.

On the other hand, it frequently happens that although some antistatic agents may have a very excellent antistatic effect, they cannot be used for photographic materials since they exert bad influences on the photographic properties of photographic silver halide emulsions, such as sensitivity, formation of fog, granularity, sharpness, etc., as well as they form scums in fix solutions. For example, it is known that polyethylene oxide series compounds, onium salts, etc., have antistatic effect but they frequently exert bad influences on photographic properties such as the increase of fog, desensitization, the reduction in granularity, etc.

In particular, in photographic materials having silver halide emulsion layers on the both sides of the supports, such as direct X-ray films, it is difficult to establish a technique of effectively imparting antistatic property to the photographic materials without reducing the photographic properties of the photographic materials.

Also, some of antistatic agents which may show a sufficient effect for the prevention of static marks immediately after coating show a reduction in antistatic faculty during the storage of, for example, medical direct X-ray films while inserting a paper between the films.

Furthermore, when the proportion of antistatic agents existing on the surfaces of photographic materials becomes relatively large, the antistatic agents are transferred to delivery rollers, cameras, screens, etc., which are brought into contact with the surfaces of the photographic materials, whereby various problems occur.

For example, when the antistatic agents are transferred to delivery rollers, they cause roller stain and cause sometimes attaching of the antistatic agents to the photographic films which passed through the rollers later.

Still further, in X-ray films the transfer of the antistatic agents causes important problems. If the antistatic agents are transferred to fluorescent intensifying screens, the screens are denatured and stains and unevenness are formed in the X-ray films after exposure, which reduces the quality of the photographic films as well as causes an erroneous diagnosis.

SUMMARY OF THE INVENTION

A first object of this invention is to provide silver halide photographic materials having improved antistatic property.

A second object of this invention is to provide a manner of imparting antistatic property to photographic materials without exerting a bad influence on the photographic properties such as sensitivity, fog formation, granularity, sharpness, etc.

A third object of this invention is to provide silver halide photographic materials which can be stored for a long period of time without greatly reducing the antistatic faculty after the production thereof.

A fourth object of this invention is to provide photographic materials which do not cause transferring of antistatic agents to delivery rollers, cameras, fluorescent intensifying screens, etc.

A fifth object of this invention is to provide photographic materials which do not form scums in fix solutions.

These objects of this invention can be attained by a silver halide photographic material comprising a support having thereon at least one gelatin-containing layer, at least one of the gelatin-containing layers containing a gelatin reactive surface active agent having at least one long chain hydrophobic group, at least one hydrophilic group selected from a cationic group, an anionic group, an amphoteric group, and a nonionic group, and at least one group reactive with gelatin in one molecule thereof.

DETAILED DESCRIPTION OF THE INVENTION

The long chain hydrophobic group of the surface active agent used in this invention may be a straight or branched chain alkyl group having 8 to 18 carbon atoms such as an octadecyl group, a dodecyl group, an octyl group, etc.; a straight chain alkenyl group having 14 to 18, preferably 18 carbon atoms such as an oleyl group (i.e., $C_{18}H_{35}$), etc.; an alkyl group substituted with a hydroxy group, a halogen atom, a nitro group or an amino group such as a 1-hydroxy-octadecyl group, etc.; an aralkyl group having 12 to 24 carbon atoms such as a dodecylphenyl group, etc.; or an aralkyl group substituted with a hydroxy group, a halogen atom, a nitro group, an amino group or a lower alkyl group having 12 to 24 carbon atoms such as an o-chloro-dodecyl-phenyl group, etc.

The hydrophilic group can be a cationic group such as a quaternary ammonium group, a phosphonium group, or a sulfonium group; an anionic group such as a sulfonic acid group, a carboxylic acid group or a phosphoric acid group; an amphoteric group such as a betaine carboxylate or betaine sulfonate; or a nonionic group such as ethylene oxide addition products, propylene oxide addition products or ethylene oxide-propylene oxide block addition products. Preferred hydrophilic groups are a cationic group, an amphoteric group, and a nonionic group.

The group reactive with gelatin is illustrated by an active vinyl group, an epoxy group, a methanesulfonic acid group, a group having an active halogen atom, an active ester group, a formyl group, a maleimido group, an acid halide group (e.g., carbonyl and sulfonyl halides), an azolido group, etc. The term "active" is with reference to the ability of the substituent to react with an amino group in the gelatin molecule in an addition or substitution reaction. Representative examples are provided below in the definition of the -C moiety in Formula (I).

In the gelatin reactive surface active agents used in this invention, it is preferred that the group reactive with gelatin be disposed at a position adjacent to the hydrophilic group of the surface active molecule.

Furthermore, the particularly preferred surface active agents used in this invention are represented by the following general formula (I):

$$R-(A)-(B)_m-(A)_n-(R_1)_l-C \quad (I)$$

wherein R represents a straight or branched chain alkyl group having 8 to 18 carbon atoms, a straight chain alkenyl group having 8 to 18 carbon atoms such as an oleyl group, a substituted alkyl group (e.g., an alkyl group substituted with a hydroxy group, a halogen atom, an amino group, a nitro group, etc.), an aralkyl group having to 24 carbon atoms such as a dodecylphenyl group, or a substituted aralkyl group (e.g., an aralkyl group substituted on the benzene ring with a hydroxy group, a halogen atom, an amino group, a nitro group, or a lower alkyl group having 1 to 8 and preferably 1 to 4 carbon atoms). R is preferably alkyl or alkenyl and most preferably alkyl.

A represents

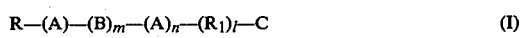

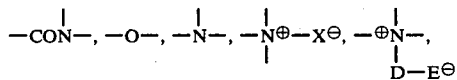

etc., wherein the counterion, $X^\ominus$, is an anion such as $Cl^\ominus$, $Br^\ominus$, $CH_3SO_4^\ominus$ and

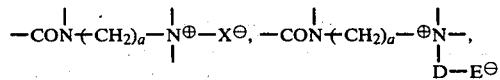

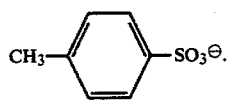

D represents a straight or branched chain alkylene group having 1 to 8 carbon atoms, preferably 1 to 4 carbon atoms or an aralkylene group having 8 to 16, preferably 8 to 12 carbon atoms; E represents a group —COO or a group —SO$_3$; and a is an integer of 2 to 8 and preferably 2 to 4. A is preferably a cationic, a betaine or nonionic group. These groups are divalent, trivalent group, or tetravalent as shown and may bear a substituent in addition to the necessary bonds in general formula (I). As the substituent, there are, for example, a hydrogen atom, an alkyl group having 1 to 18, preferably 1 to 12, more preferably 1 to 8 carbon atoms, a substituted alkyl group having 1 to 18, preferably 1 to 12, more preferably 1 to 8 carbon atoms (e.g., an alkyl group substituted with a hydroxy group, a halogen atom, etc.), or a

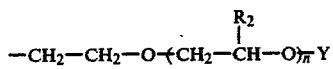

group wherein n is an integer of 3 to 50, preferably 5 to 30; Y represents a hydrogen atom, or an alkyl group having 1 to 18, preferably 1 to 12, more preferably 1 to 6 carbon atoms; and R$_2$ represents a hydrogen atom, a methyl group, or an ethyl group and may be different in each repeating unit.

Also, in the general formula, B represents a group of the formula

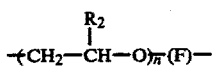

wherein n is an integer of 3 to 50, particularly preferably 5 to 30 and (F) represents a simple bond or a straight chain alkylene group having 1 to 18, preferably 2 to 12, more preferably 2 to 8 carbon atoms;

R$_1$ represents a straight chain alkylene group having 1 to 18, preferably 1 to 4 carbon atoms;

The C moiety reacts with the gelatin and represents an active vinyl group, an epoxy group, a methane-sulfonic acid group, a group having active halogen atom, an active ester group, a formyl group, a maleimido group, an acid halide group, an azolido group, etc., such as a —Z—CH=CH$_2$ group (wherein Z represents —CO—, —NHCO—, or —SO$_2$—),

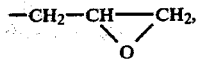

—OSO$_2$—CH$_3$, —COCH$_2$G (wherein G represents a halogen atom, preferably F or Cl), —COOCH$_2$G,

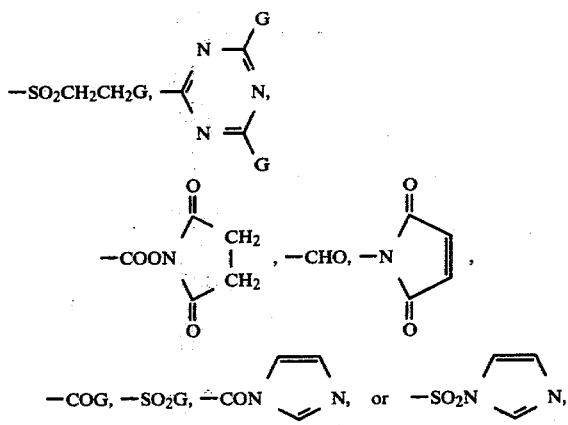

—COG, —SO$_2$G, —CON⌐N, or —SO$_2$N⌐N, although the invention is not limited to these groups but includes any group which is reactive with gelatin. In the above-described groups, an active vinyl group, an epoxy group, a methanesulfonic acid group, an active ester group, a maleimido group, and a group having an active halogen are preferred from the standpoint of facilitating preparation of the surface active agent, facilitating handling, and reactivity with gelatin.

l, m and n each is 0 or 1.

It is preferred that the gelatin reactive surface active agent of this invention possesses a surface tension of not more than 40 dynes/cm, particularly not more than 35 dynes/cm as an aqueous 1.0% by weight solution thereof.

Practical examples of these compounds are illustrated below but the invention is not limited to these compounds alone.

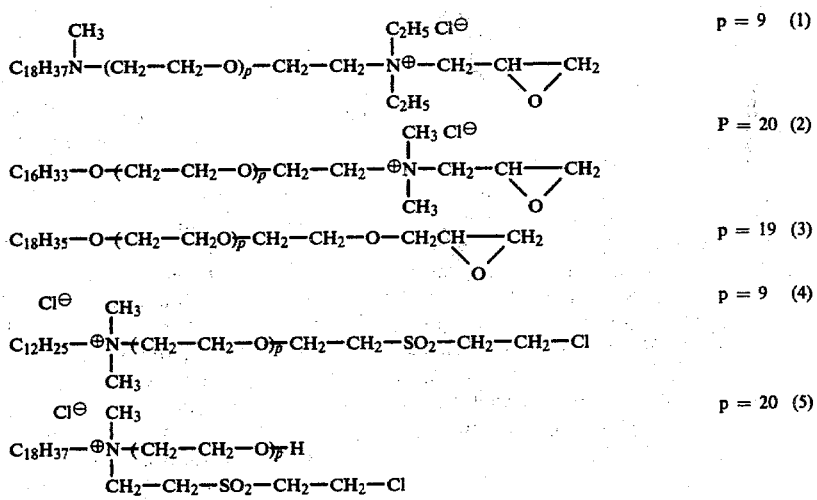

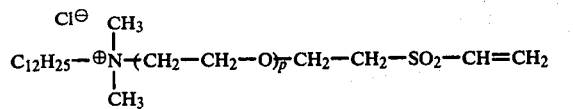

p = 9  (6)

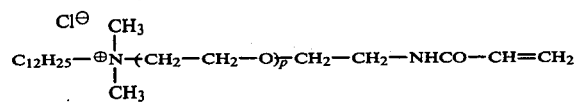

p = 9  (7)

p = 19  (8)

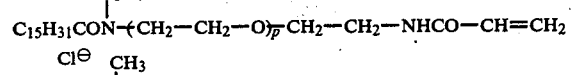

p = 9  (9)

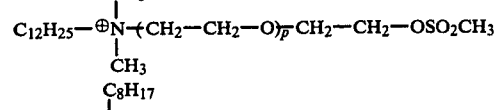

(10)

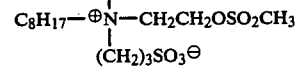

p = 9  (11)

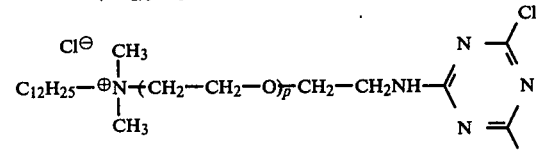

p = 9  (12)

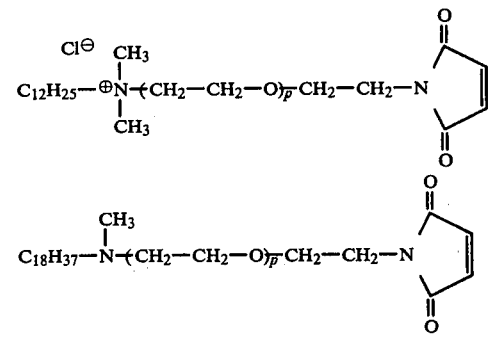

p = 19  (13)

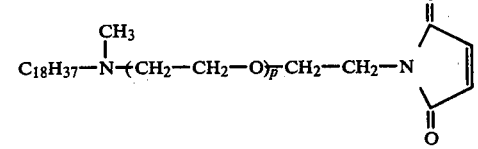

p = 9  (14)

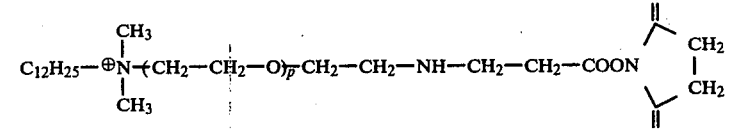

These gelatin reactive surface active agents used in this invention are prepared by introducing reactive groups with reference to the descriptions of, for example, Japanese Patent Application (OPI) Nos. 74832/73 (The term "OPI" as used herein refers to a "published unexamined Japanese patent application") and 126124/76, Japanese Patent Publication No. 41608/76, British Pat. No. 1,071,298, U.S. Pat. No. 2,992,109, *Yu Kagaku* (*Oil Chemistry*), Vol. 67, No. 4, 592 (1964), and *Organic Synthesis Collective Volume*, Vol. 5, 944 (1973). Compounds having substituents effective for introducing reactive groups as described in the above references can be prepared by the processes described in, for example, *Journal of the Chemical Society*, 684 (1942), ibid., 99 (1943), ibid., 3650 (1950), *Journal of the American Chemical Society*, Vol. 54, 1499 (1932), ibid., Vol. 54, 3441 (1932), ibid., Vol. 61, 3585 (1932), *Organic Reactions*, Vol. 8, 197 (1954), and *Chemistry Letter*, 577 (1975) (for example, by substituting a halogen atom for a hydroxy group or substituting an amino group for a halogen group).

The following examples illustrate processes for producing several gelatin reactive surface active agents used in this invention.

SYNTHESIS EXAMPLE 1

Synthesis of Compound (1)

In a three neck flask was placed 102 g (1.1 mols) of epichlorohydrin and while stirring vigorously, 73 g (1 mol) of diethylamine was added dropwise to epichlorohydrin together with a small amount (1/10 mol of the amine) of water at temperatures below 25° C. Thereafter, the mixture was stirred for 5 hours at 30° to 35° C. Then, an aqueous 35 to 40% solution of 1.7 mols of sodium hydroxide was added dropwise to the mixture at 25° to 30° C. followed by stirring vigorously. Thereafter, the mixture was further stirred for 3 hours at the same temperature as above. Then, after cooling the mixture, 200 ml of water was added to the reaction mixture to dissolve the salts formed and after further adding 300 ml of ether to the mixture and shaking them, the resultant mixture was allowed to stand, thereby the reaction mixture was separated into two phases. The organic phase thus formed was collected and dried with the addition of granular potassium hydroxide. Then, ether was distilled away and the residue was distilled under reduced pressure in $N_2$ stream to provide 77 g of diethylglycidylamine having a boiling point of 50° to 52° C./13 mmHg).

Then, 72.3 g (0.1 mol) of

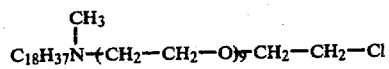

(prepared from

and thionyl chloride) was mixed with 14.2 g (0.11 mol) of diethylglycidylamine prepared in the above-described procedure together with 30 ml of acetone and the mixture was stirred for 2 hours at 25° to 30° C. to cause reaction.

After the reaction was over, excessive diethylglycidylamine was distilled away under reduced pressure (lower than 10 mmHg) and the remaining viscous liquid was identified by a conventional analysis. The yeild of the product was 88%.

SYNTHESIS EXAMPLE 2

Synthesis of Compound (4)

To a solution of 88 g (0.85 mol) of sodium hydrogensulfite in 400 ml of water were added dropwise 131 g (0.82 mol) of β-chloroethanesulfonyl chloride and a solution of 88 g of sodium hydroxide in 240 ml of water simultaneously at about 5° C. After 30 minutes, 80 g of an aqueous solution of 50% sulfuric acid was added dropwise to the mixture and after stirring them for 1 hour, the reaction mixture was filtered. To the filtrate was added dropwise a dispersion of 581 g (0.82 mol) of

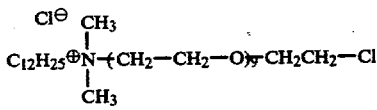

in 1 liter of water at temperatures below 10° C. and the mixture was allowed to stand for about 3 days under cooling. Then, the reaction mixture was concentrated under reduced pressure to about half. The crystals thus precipitated were recovered by filtration and recrystallized from ethanol to provide 470 g of Compound (4) as white crystals. The yield was 72%.

SYNTHESIS EXAMPLE 3

Synthesis of Compound (5)

In 500 ml of acetonitrile was dissolved 116 g (0.1 mol) of

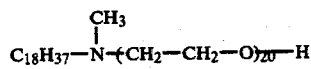

and then a solution of 19 g (0.1 mol) of bischloroethylsulfone in 100 ml of acetonitrile was added dropwise to the solution at 20° C. After stirring the mixture for 10 hours, the solvent was distilled away to provide 128 g of Compound (5) as a white solid. The yield was 78%.

SYNTHESIS EXAMPLE 4

Synthesis of Compound (6)

In 200 ml of acetonitrile was dissolved 39.6 g (49.5 millimols) of Compound (4) obtained in Synthesis Example 2 and while stirring the solution, a solution of 5 g (49.5 millimols) of triethylamine in 50 ml of acetonitrile was added dropwise to the solution at 0° C. Thereafter the mixture was stirred for 5 hours at room temperature. Then, after filtering off the triethylamine hydrochloride thus precipitated, the filtrate was concentrated under reduced pressure and the residue formed was washed with a small amount of water and dried to provide 30 g of Compound (6) as wax-like solid. The yield was 79%. It was confirmed by infrared spectral analysis that the solid product showed a sharp absorption at 1,600 cm$^{-1}$ and thus had a vinylsulfone structure.

SYNTHESIS EXAMPLE 5

Synthesis of Compound (7)

To a solution of 9.1 g (0.1 mol) of acrylic acid chloride in 200 ml of acetonitrile was added dropwise a solution of 69 g (0.1 mol) of

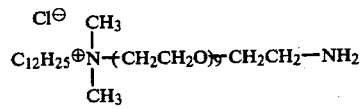

(obtained by aminating the corresponding chloride) in 300 ml of acetonitrile at 0° C. After stirring the mixture for 1 hour, the solvent and chloric acid by-product were distilled away under reduced pressure to provide 73 g of Compound (7) as white wax-like solid. The yield was 98%.

SYNTHESIS EXAMPLE 6

Synthesis of Compound (8)

The desired product was prepared from

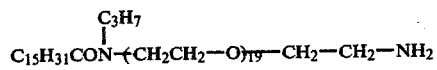

as in Synthesis Example 5. The product was a light yellow wax-like solid and the yield was 95%.

SYNTHESIS EXAMPLE 7

Synthesis of Compound (11)

In 200 ml of acetonitrile was dissolved 28.5 g (0.1 mol) of $(C_8H_{17})_2NCH_2CH_2OH$ and then 11.5 g (0.1 mol) of methanesulfonyl chloride was added dropwise to the solution with stirring at 10° C. Then, after stirring the mixture for 3 hours at temperatures below 20° C., the reaction mixture was neutralized carefully with a solution of 4 g (0.1 mol) of sodium hydroxide in 40 ml of water. After concentrating the reaction mixture under reduced pressure, the residue was dispersed in 1 liter of water and the product was extracted with 500 ml of ether. The organic layer obtained was dried by anhydrous magnesium sulfate and then ether was distilled away to provide 27.0 g of $(C_8H_{17})_2NCH_2CH_2OSO_2CH_3$.

Then, in 200 ml of acetonitrile was dissolved 20 g (55.1 millimols) of $(C_8H_{17})_2NCH_2CH_2OSO_2CH_3$ and then a solution of 6.7 g (55.1 millimols) of propanesultone in 100 ml of acetonitrile was added dropwise to the solution at 20° C. After stirring the mixture for 1 hour, the solvent was distilled away under reduced pressure to provide 25.9 g of Compound (10) as white solid. The yield was 97%.

SYNTHESIS EXAMPLE 8

Synthesis of Compound (13)

In 500 ml of acetonitrile was dissolved 116 g (0.1 mol) of

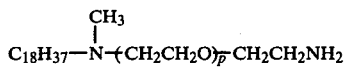

(wherein p is 19) and then 9.8 g (0.1 mol) of maleic anhydride was added thereto in several steps with stirring at 20° C. After further stirring the mixture for 1 hour, 35 ml of acetic anhydride and 3.3 g of anhydrous sodium acetate were added to the mixture and the resultant mixture was heated on a steam bath for 30 minutes. After distilling away the solvent, the residue was recrystallized from ethanol to provide 89 g of Compound (13) as white crystals. The yield was 70%.

In this invention, the compound shown by general formula (I) is incorporated in at least one of the gelatin-containing layers.

As the gelatin-containing layers, there are silver halide emulsion layers, interlayers, surface protective layers, back layers, etc., but it is preferred to incorporate the compound of this invention in a surface protective layer or a back layer which is the outermost layer constituting a photographic material or in an interlayer which becomes the outermost layer at the production of photographic material.

In particular, when the compound of this invention is incorporated in the surface protective layers of photographic materials, the most desirable effect of this invention is obtained.

For applying the compounds of general formula (I) used in this invention to photographic materials, the compound is dissolved in an organic solvent such as methanol, isopropanol, acetone, etc., or a mixture thereof, the solution of the compound is added to a coating composition for forming silver halide emulsion layer, in interlayer, a protective layer, etc., and the coating composition is coated by dip coating, air knife coating or extrusion coating using the hopper as described in U.S. Pat. No. 2,681,294 or further the coating compositions prepared by the same way as above are simultaneously coated as two or more layers by the method described in U.S. Pat. Nos. 3,508,947, 2,941,898, 3,526,528, etc.

The compound of this invention is preferably used in an amount of about 0.1 to 10 g, particularly about 0.5 to 7 g per 100 g of gelatin.

As supports for photographic materials used in this invention, there are cellulose nitrate films, cellulose acetate films, cellulose acetate butyrate films, cellulose acetate propionate films, polystyrene films, polyethylene terephthalate films, polycarbonate films, laminates of these films, thin glass sheets, papers, etc. Furthermore, papers laminated or coated with baryta or α-olefin polymers, in particular, a polymer of an α-olefin having 2 to 10 carbon atoms, such as polyethylene, polypropylene, ethylene-butene copolymer, etc.

The gelatin-containing layer containing the compound of this invention may contain as a binder a protein such as colloidal albumin, casein, etc.; a cellulose compound such as carboxymethyl cellulose, hydroxyethyl cellulose, etc.; a sugar derivative such as agar agar, sodium alginate, a starch derivative, etc.; or a synthetic hydrophilic colloid such as polyvinyl alcohol, poly-N-vinylpyrrolidone, polyacrylic acid copolymer, polyacrylamide, and the derivatives or partially hydrolyzed products of these polymers in addition to gelatin.

Gelatin used in this invention can be so-called lime-processed gelatin, acid-processed gelatin, and enzyme-processed gelatin. Gelatin may be partially or wholly replaced with a synthetic polymer or may be replaced with a so-called gelatin derivative, i.e., a gelatin modified by a reagent having one group reactive with an amino group, an imino group, a hydroxy group or a carboxy group contained in the molecule thereof as a functional group or a graft polymer formed by bonding the molecular chain of a polymer to gelatin.

There are no particular limitations about the kind of silver halides, method of preparation of silver halides, chemical sensitization for the silver halides, antifoggants, stabilizers, hardening agents, antistatic agents, plasticizers, lubricants, coating aids, matting agents, whitening agents, spectral sensitizing dyes, dyes, color couplers, etc.; used in the silver halide emulsion layers, surface protective layers of the photographic materials of this invention and they are described in, for example, *Product Licensing*, Vol. 92, 107–110 (December, 1971) and *Research Disclosure*, Vol. 176, 22–31 (December, 1978).

In particular, as the antifoggants or stabilizers, there are heterocyclic compounds such as 4-hydroxy-6-methyl-1,3,3a,7-tetrazaindene-3-methyl-benzothiazole, 1-phenyl-5-mercaptotetrazole, etc., mercury-containing compounds, mercapto compounds, gold salts, etc., and as the hardening agents, there are aldehyde series compounds such as mucochloric acid, mucobromic acid, mucophenoxychloric acid, mucophenoxybromic acid, formaldehyde, dimethylolurea, trimethylolmelamine, glyoxal, monomethylglyoxal, 2,3-dihydroxy-1,4-dioxane, 2,3-dihydroxy-5-methyl-1,4-dioxane, succinaldehyde, 2,5-dimethoxytetrahydrofuran, glutaraldehyde, etc.; active vinylic compounds such as divinylsulfone, methylenebismaleimide, 5-acetyl-1,3-diacryloyl-hexahydro-s-triazine, 1,3,5-triacryloylhexahydro-s-triazine, 1,3,5-trivinylsulfonyl-hexahydro-s-triazine-bis(vinylsulfonylmethyl) ether, 1,3-bis(vinylsulfonylmethyl)-propanol-2, bis(α-vinylsulfonylacetamido)ethane, etc.; active halogen series compounds such as 2,4-dichloro-6-hydroxy-s-triazine.sodium salt, 2,4-dichloro-6-methoxy-s-triazine, 2,4-dichloro-6-(4-sulfoanulino)-s-triazine.sodium salt, 2,4-dichloro-6-(2-sulfoethylamino)-s-triazine, N,N'-bis(2-chloroethylcarbamyl)piperazine, etc.; epoxy series compounds such as bis(2-epoxypropyl)methylpropylammonium.p-toluenesulfonate, 1,4-bis(2',3'-epoxypropyloxy)butane, 1,3,5-triglycidyl isocyanurate, 1,3-diglycidyl-5-(γ-acetoxy-β-oxypropyl) isocyanurate, etc.; ethyleneimine series compounds such as 2,4,6-triethyleneimino-s-triazine, 1,6-hexamethylene-N,N'-bisethylene urea, bis-β-ethyleneiminoethyl thioether, etc.; methanesulfonic acid ester series compounds such as 1,2-di(methanesulfonoxy)ethane, 1,4-di(methanesulfonoxy)pentane, etc.; carbodiimide series compounds such as dicyclohexycarbodiimide, 1-cyclohexyl-3-(3- trimethylaminopropyl)carbodiimide.p-toluenesulfonate, 1-ethyl-3-(3-dimethylaminopropyl)carbodiimide.hydrochloride, etc.; isoöxazole series compounds such as 2,5-dimethylisoöxazole.perchlorate, 2-ethyl-5-phenylisoöxazole-3'-sulfonate, 5,5'-(paraphenylene)-bisisoöxazole, etc.; and inorganic compounds such as chromium alum, chromium acetate, etc.

Depending on the number of amino groups in the gelatin and the amount of the compound of this invention, the amount of the hardening agent is about 0.01 to 10 g, preferably about 0.1 to 5 g per 100 g of gelatin.

The photographic layers constituting the photographic materials of this invention may further contain known surface active agents alone or as a mixture thereof. As the surface active agents used, there are natural surface active agents such as saponin, etc.; nonionic surface active agents such as alkylene oxide series surface active agents, glycerol series surface active agent, glycidol series surface active agent, etc.; cationic surface active agents such as higher alkylamines, quaternary ammonium salts, pyridine and other heterocyclic compounds, phosphoniums or sulfoniums, etc.; anionic surface active agents having acid groups such as carboxylic acid, sulfonic acid, phosphoric acid, sulfuric acid ester, phosphoric acid ester groups, etc.; and amphoteric surface active agents such as aminoacids, aminosulfonic acids, sulfonic acid or phosphoric acid esters of aminoalcohols, etc.

The photographic materials of this invention may further contain in their constituting layers, the alkylacrylate series latexes described in U.S. Pat. Nos. 3,411,911 and 3,411,912 and Japanese Patent Publication No. 5331/70 and also silica or polymethyl acrylate as a matting agent.

Also, in this invention, an enhanced effect for the prevention of static marks is obtained by using fluorine surface active agents together with the compound of this invention. Examples of these fluorine surface active agents are the fluorine surface active agents described in, for example, British Pat. Nos. 1,330,356 and 1,524,631, U.S. Pat. Nos. 3,666,478 and 3,589,906, Japanese Patent Publication No. 26687/77 and Japanese Patent Application (OPI) Nos. 46733/74 and 32322/76. Typical examples of the fluorine surface active agents are, for example, N-perfluorooctylsulfonyl-N-propylglycine potassium salt, 2-(N-perfluorooctylsulfonyl-N-ethylamino)ethyl phosphate, N-[4-perfluorononyloxy)-benzyl]-N,N-dimethylammonio acetate, N-[3-(N',N',N'-trimethylammonio)propyl]perfluorooctylsulforamido iodide, N-(polyoxyethylenyl)-N-propyl perfluorooctyl-sulforamido $(C_3F_7SO_2N(C_3H_7)(CH_2CH_2O)_nH)$, and fluorine-containing succinic acid series compounds. Suitable and preferred amounts for the fluorine surface active agents are about 1 to 100 and particularly about 5 to 20% by weight based on the compound of the general formula (I).

The invention will now be further described by referring to the following examples. These examples should not be considered limiting. Unless otherwise indicated all parts and percents are by weight.

EXAMPLE 1

Each of samples 1 to 11 was prepared by coating both surfaces of a polyethylene terephthalate film of about 175 microns thick with silver halide emulsion layers and protective layers in order according to a conventional manner and drying the layers. The compositions of the layers were as follows.

Silver Halide Emulsion Layer: about 5 microns thick.
Binder: 2.5 g/m² of gelatin.
Coated Amount of Silver: 5 g/m².
Silver Halide Composition: 1.5 mol% of AgI and 98.5 mol% AgBr.
Hardening Agent: 0.4 g/100 g gelatin of 2,4-dichloro-6-hydroxy-1,3,5-triazine.sodium salt.
Antifoggant: 0.5 g/100 g Ag of 1-phenyl-5-mercaptotetrazole.
Protective Layer: about 1 micron thick.
Binder: 1.7 g/m² of gelatin and 0.3 g/m² of potassium polystyrenesulfonate (mean mol. weight of about 70,000).
Coating Agent: 7 mg/m² of N-oleoyl-N-methyltaurine sodium salt.

In this example, however, sample 1 was composed of the above-described compositions only and samples 2 to 8 contained Compounds (1), (4), (6), (7), (10), (11) and (14), respectively, in the protective layers in addition to the above-described compositions for the layers. Furthermore, for the sake of comparison, samples 9 to 11 were prepared by adding following comparison compounds A, B and C, respectively, in place of the compounds of this invention in the protective layers in addition to the above-described compositions.

Comparison Compound A:
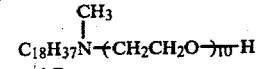
Comparison Compound B:
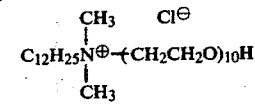
Comparison Compound C:

Antistatic property of these samples was determined by the following method. After humidifying each of the unexposed samples at 25° C. and 25% RH for 2 hours, the sample was rubbed by a Neoprene rubber roller at one of the emulsion-coated surface in a dark room under the same humidity conditions as above, developed by a developer having the composition shown below, fixed, and washed. Thereafter, the occurrence of static marks was inspected.

Also, the change of antistatic effect with the passage of time was determined in the following manner. That is, after humidifying each of the samples and the insertion papers used below for 1 hour at 25° C. and 70% RH, each of the samples was closed in a container made of a black paper laminated with polyethylene in the state that the insertion paper was inserted between the samples in a dark room under the same humidity conditions as above and stored for 2 weeks at room temperature.

Thereafter, each sample was rubbed by a Neoprene rubber roller at the emulsion-coated surface thereof in a dark room under conditions of 25° C. and 25% RH, developed by the developer having the following composition, fixed, and washed with water. Then, the occurrence of static marks in the samples thus stored was inspected.

The composition of the developer used in the above development was as follows:

| Developer Composition: | |
|---|---|
| Warm Water | 800 ml |
| Sodium Tertapolyphosphate | 2.0 g |
| Anhydrous Sodium Sulfite | 50 g |
| Hydroquinone | 10 g |
| Sodium Carbonate (monohydrate) | 40 g |
| 1-phenyl-3-pyrazolidone | 0.3 g |
| Potassium Bromide | 2.0 g |
| Water to make | 1,000 ml (ph 10.2) |

On the other hand, each of other unexposed samples was exposed to a tungsten lamp through Filter-SP-14 made by Fuji Photo Film Co., Ltd. at an exposure amount of 1.6 CHM, developed by a developer having the above-mentioned composition for 30 seconds at 35° C., fixed, and washed with water. Thereafter, the sensitivity and the formation of fog were measured.

Also, apart from this, each of the still unexposed samples was stored for 3 days at 50° C. and then exposed and processed under the same conditions as above. Thereafter, the sensitivity and the formation of fog were also measured to determine the influences of the added compounds on the photographic properties.

The results of determining the antistatic property and the photographic properties of these samples are shown in Table 1.

TABLE 1

| Sample No. | Antistatic Agent | Antistatic Property* After coating | Antistatic Property* After Storage | Photographic Property After Coating Fog | Photographic Property After Coating Sensitivity | Photographic Property After Storage Fog | Photographic Property After Storage Sensitivity |
|---|---|---|---|---|---|---|---|
| 1 | None (control) | D | D | 0.16 | 0 | 0.17 | −0.01 |
| 2 | Compound (1) of the invention | A | A | 0.16 | 0 | 0.16 | −0.01 |
| 3 | Compound (4) of the invention | A | A | 0.16 | 0 | 0.16 | −0.01 |
| 4 | Compound (6) of the invention | A | A | 0.16 | 0 | 0.17 | −0.01 |
| 5 | Compound (7) of the invention | A | B | 0.17 | 0 | 0.17 | −0.02 |
| 6 | Compound (10) of the invention | A | B | 0.16 | 0 | 0.17 | −0.02 |
| 7 | Compound (11) of the invention | A | A | 0.16 | 0 | 0.16 | −0.01 |
| 8 | Compound (14) of the invention | A | A | 0.16 | 0 | 0.16 | −0.01 |
| 9 | Compound A (comp.) | A | D | 0.22 | −0.07 | 0.37 | −0.20 |
| 10 | Compound B (comp.) | A | D | 0.23 | −0.05 | 0.35 | −0.16 |
| 11 | Compound C (comp.) | B | D | 0.28 | +0.02 | 0.45 | evaluation impossible |

*: Antistatic property was evaluated by the occurrence of static marks:
A: The occurrence of static marks is not observed.
B: The occurrence of static marks is slightly observed.
C: The occurrence of static marks is considerably observed.
D: The occurrence of static marks is observed over almost the entire surface.

Also, the sensitivity value in the above table is the deviation from a standard sensitivity shown by the absolute value of log E, the sensitivity of the control sample (sample 1) immediately after coating being taken as the standard sensitivity and no deviation from the standard sensitivity shows that there was no influence on the photographic properties.

As is clear from Table 1, the samples imparted with antistatic property using the gelatin reactive surface active agents of this invention had excellent antistatic effect immediately after coating and the antistatic property was not reduced when the samples were stored for a long period of time.

Furthermore, it is understood that the addition of the gelatin reactive surface active agents of this invention to photographic materials do not exert bad influence on the photographic properties after coating as well as after storing the photographic materials for a long period of time. On the other hand, in the case of using the comparison compounds, the antistatic effect was greatly reduced with the passage of time and the compounds exerted bad influences on the photographic properties.

EXAMPLE 2

Each of samples 12 to 18 was prepared by coating, in succession, a cellulose triacetate film support with an antihalation layer, a red sensitive silver halide emulsion layer, an interlayer, a green sensitive silver halide emulsion layer, a yellow filter layer, a blue sensitive silver halide emulsion layer, and a protective layer according to a conventional manner and drying the layers. The compositions of the layers were as follows:

Antihalation Layer:
Binder: 4.4 g/m$^2$ of gelatin.
Hardening Agent: 1.2 g/100 g gelatin of 1,3-bis-vinylsulfonyl)propanol-2.
Coating Aid: 4 mg/m$^2$ of sodium dodecylbenzenesulfonate.
Antihalation Agent: 0.4 g/m$^2$ of blach colloid silver.
Red Sensitive Silver Halide Emulsion Layer:
Binder: 7 g/m$^2$ of gelatin.
Hardening Agent: 1.2 g/100 g gelatin of 1,3-bis(vinylsulfonyl)propanol-2.
Coating Aid: 10 mg/m$^2$ of sodium dodecylbenzenesulfonate.
Coated Amount of Silver: 3.1 g/m$^2$.
Silver Halide Composition: 2 mol% of AgI and 98 mol% of AgBr.
Antifoggant: 0.9 g/100 g Ag of 4-hydroxy-6-methyl-1,3,3a,7-tetrazaindene.
Coupler: 38 g/100 g Ag of 1-hydroxy-4-(2-acetylphenyl)azo-N-[4-(2,4-di-tert-amylphenoxy)butyl]-2-naphthamide.
Sensitizing Dye: 0.3 g/100 g Ag of anhydro-5,5'-dichloro-9-ethyl-3,3'-di(3-sulfopropyl)thiacarboxyanilinehydroxide.pyridinium salt.
Interlayer:

Binder: 2.6 g/m² of gelatin.
Hardening Agent: 1.2 g/100 g gelatin of 1,3-bis(vinylsulfonyl)propanol-2.
Coating Aid: 12 mg/m² of sodium dodecylbenzenesulfonate.
  Green Sensitive Silver Halide Emulsion Layer:
Binder: 6.4 g/m² of gelatin.
Hardening Agent: 1.2 g/100 g gelatin of 1,3-bis(vinylsulfonyl)propanol-2.
Coating Aid: 9 mg/m² of sodium dodecylbenzenesulfonate.
Coated Amount of Silver: 2.2 g/m².
Silver Halide Composition: 3.3 mol% of AgI and 96.7 mol% of AgBr.
Stabilizer: 0.6 g/100 g Ag of 4-hydroxy-6-methyl-1,3,3a,7-tetrazaindene.
Coupler: 37 g/100 g Ag of 1-(2,4,6-trichlorophenyl)-3-{3-[(2,4-di-tert-amylphenoxy)acetoazido]benzamido}-4-(4-methoxyphenyl)azo-5-pyrazolone.
Sensitizing Dye: 0.3 g/100 g Ag of anhydro-5,5'-diphenyl-9-ethyl-3,3'-di(2-sulfoethyl)oxacarbocyaninehydroxy.puridinium salt.
  Yellow Filter Layer:
Binder: 2.3 g/m² of gelatin.
Filter Component: 0.7 g/m² of yellow colloid silver.
Hardening Agent: 1.2 g/100 g gelatin of 1,3-bis(vinylsulfonyl)propanol-2.
Surface Active Agent: 7 mg/m² of 2-sulfonatosuccinic acid bis(2-ethylhexyl)ester.sodium salt.
  Blue Sensitive Silver Halide Emulsion Layer:
Binder: 7 g/m² of gelatin.
Hardening Agent: 1.2 g/100 g gelatin of 1,3-bis(vinylsulfonyl)propanol-2.
Coating Aid: 8 mg/m² of sodium dodecylbenzenesulfonate.
Coated Amount of Silver: 2.2 g/m².
Silver Halide Composition: 3.3 mol% AgI and 96.7 mol% AgBr.
Stabilizer: 0.4 g/100 g Ag of 4-hydroxy-6-methyl-1,3,3a,7-tetrazaindene.
Coupler: 45 g/100 g Ag of 2'-chloro-5'-[2-(2,4-di-tert-aminophenoxy)butyramido]-α-(5,5'-dimethyl-2,4-dioxo-3-oxazolidinyl)-α-(4-methoxybenzoyl)acetanilide.
  Protective Layer:
Binder: 2 g/m² of gelatin and 0.3 g/m² of a styrene-maleic anhydride copolymer (1:1) having a mean molecular weight of about 100,000.
Hardening Agent: 1.2 g/100 g binder of 1,3-bis(vinylsulfonyl)propanol-2.
Coating Aid: 5 mg/m² of sodium dioctylsulfosuccinate.

In this example, however, sample 12 was composed of the above-described compositions only and samples 13 to 18 contained in the protective layers Compounds (1), (4), (8) and (13) of this invention and Comparison Compounds A and B shown in Example 1, respectively, in an amount of 100 ml/m² in addition to the aforesaid composition for the protective layer.

The antistatic property and the photographic properties were determined in the same manner as in Example 1 except that an ordinary color development processing was employed in place of the black-and-white development in Example 1. The results are shown in Table 2.

TABLE 2

| Sample No. | Antistatic Agent | Occurrence of Static Mark | |
|---|---|---|---|
| | | After Coating | After Storage |
| 12 | None (control) | D | D |
| 13 | Compound (1) (invention) | A | A |
| 14 | Compound (4) (invention) | A | A |
| 15 | Compound (8) (invention) | A | B |
| 16 | Compound (13) (invention) | A | A |
| 17 | Compound A (comparison) | B | D |
| 18 | Compound B (comparison) | B | D |

Evaluation A, B and D have the same meaning as in Table 1.

As is clear from Table 2, it is understood that the samples using the compounds of this invention did not show reduction in antistatic property when they were stored for a long period of time. On the other hand, the samples using the comparison compounds showed great reduction in antistatic property with the passage of time. Also, when the samples were exposed according to the method by JIS and subjected to ordinary color development processing, samples 17 and 18 using the comparison compounds showed great desensitization and increase in the formation of fog in the blue, green and red sensitive silver halide emulsion layers, while the samples using the compounds of this invention scarcely showed bad influence on the photographic properties.

EXAMPLE 3

Each of samples 19 to 29 was prepared by coating one surface of a cellulose triacetate film support with a back layer and a back protective layer having the compositions shown below and also the opposite surface of the support with the silver halide emulsion layer having the same composition as the control sample (sample 1) in Example 1.
  Back Layer:
Binder: 6.2 g/m² of gelatin.
Salt: 0.1 g/m² of potassium nitrate.
Hardening Agent: 1.2 g/100 g gelatin of 1,3-bis(vinylsulfonyl)propanol-2.
  Back Protective Layer:
Binder: 2.2 g/m² of gelatin.
Matting Agent: 20 mg/m² of polymethyl methacrylate (mean grain size of 2.5 microns).
Hardening Agent: 1.2 g/100 g gelatin of 1,3-bis(vinylsulfonyl)propanol-2.
Coating Aid: 40 mg/m² of sodium dioctylsulfosuccinate.

In this example, sample 19 was composed of the above-described compositions only and samples 20 to 29 contained the compounds of this invention and comparison compounds, respectively, in the back layers in an amount of 80 mg/m² in addition to the above-described compositions for the back layer.

The antistatic property of the back surface of each of the samples was determined by the same manner as in Example 1 except that the back surface of the sample was rubbed by a Neoprene rubber. The results are shown in Table 3.

TABLE 3

| Sample No. | Antistatic Agent | Antistatic Property | |
|---|---|---|---|
| | | After Coating | After Storage |
| 19 | None (control) | D | D |

TABLE 3-continued

| Sample No. | Antistatic Agent | Antistatic Property After Coating | After Storage |
|---|---|---|---|
| 20 | Compound (1) (invention) | A | A |
| 21 | Compound (5) (invention) | A | A |
| 22 | Compound (6) (invention) | A | A |
| 23 | Compound (8) (invention) | A | B |
| 24 | Compound (10) (invention) | A | A |
| 25 | Compound (11) (invention) | A | A |
| 26 | Compound (14) (invention) | A | A |
| 27 | Compound A (comparison) | A | D |
| 28 | Compound B (comparison) | A | D |
| 29 | Compound C (comparison | A | D |

From Table 3, it is understood that the compounds of this invention were also effective in case of using in the back layers as well as the samples using the compounds of this invention did not show reduction in antistatic property with the passage of time.

EXAMPLE 4

Each of the photographic materials having the same constitutions as sample 1 in Example 1 was immersed in an aqueous solution of 0.5% by weight of the compound shown in Table 4 for 5 seconds and then was allowed to dry under the conditions of 25° C. and 65% RH.

Each of these samples was determined about the antistatic property by the same manner as in Example 1. The results are shown in Table 4.

TABLE 4

| Sample No. | Anitstatic Agent | Antistatic Property After Coating | After Storage |
|---|---|---|---|
| 30 | None (control) | D | D |
| 31 | Compound (2) (invention) | A | A |
| 32 | Compound (5) (invention) | A | A |
| 33 | Compound (6) (invention) | A | A |
| 34 | Compound (11) (invention) | A | A |
| 35 | Compound (14) (invention) | A | A |
| 36 | Compound A (comparison) | A | D |
| 37 | Compound B (comparison) | A | D |
| 38 | Compound C (comparison) | A | D |

As is clear from Table 4, it is understood that when the compounds of this invention were applied to photographic materials by immersion coating of the aqueous solution of them, they were effective for static prevention as well as the reduction in antistatic property of the photographic materials with the passage of time could be also prevented.

While the invention has been described in detail and with reference to specific embodiments thereof, it will be apparent to one skilled in the art that various changes and modifications can be made therein without departing from the spirit and scope thereof.

What is claimed is:

1. A silver halide photographic material comprising a support having thereon at least a gelatin-containing layer containing a gelatin-reactive surface active agent having at least one long chain hydrophobic group, at least one hydrophilic group selected from a cationic group, an anionic group, an amphoteric group, and a nonionic group, and at least one group reactive with gelatin in the molecule thereof.

2. The silver halide photographic material as claimed in claim 1, wherein said gelatin-reactive surface active agent is a compound represented by the formula (I):

$$R-(A)-(B)_m-(A)_n-(R_1)_l-C \quad (I)$$

wherein R represents an alkyl group having 8 to 18 carbon atoms, an alkenyl group having 8 to 18 carbon atoms, a substituted alkyl group, an aralkyl group having 12 to 24 carbon atoms or a substituted aralkyl group; A represents

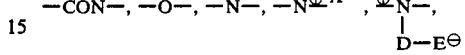

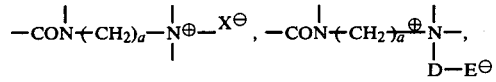

etc., wherein the counterion, $X^{\ominus}$, is an anion such as $Cl^{\ominus}$, $Br^{\ominus}$, $CH_3SO_4^{\ominus}$ and

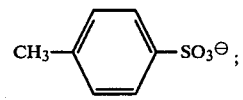

D represents an alkylene group having 1 to 8 carbon atoms or an aralkylene group having 8 to 16 carbon atoms and E represents —COO or a SO$_3$ group and a is an integer of 2 to 8; B represents a group of the formula

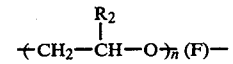

wherein n is an integer of 3 to 50 and (F) represents a simple bond or an alkylene group having 1 to 18 carbon atoms and R$_2$ represents a hydrogen atom, a methyl group or an ethyl group; R$_1$ represents an alkylene group having 1 to 8 carbon atoms; C represents an active vinyl group, an epoxy group, a methanesulfonic acid group, a group having an active halogen atom, an active ester group, an aldehyde group, a maleimido group, an acid halide group, or an azolido group; and l; m and n each is 0 or 1.

3. The silver halide photographic material as claimed in claim 1, wherein the gelatin-containing layer is a surface protective layer.

4. The silver halide photographic material as claimed in claim 1, wherein the gelatin-containing layer is a back layer.

5. The silver halide photographic material as claimed in claim 1, wherein the gelatin-containing layer is an interlayer.

6. The silver halide photographic material as claimed in claim 1, wherein the gelatin-containing layer is a silver halide emulsion layer.

7. The silver halide photographic material as claimed in claim 1, wherein the proportion of the gelatin-containing surface active agent contained in said gelatin-containing layer is about 0.1 to 10 g per 100 g of gelatin.

8. The silver halide photographic material as claimed in claim 1, wherein said gelatin-containing layer also contains a fluorine series surface active agent.

* * * * *